United States Patent [19]
Matsuura et al.

[11] Patent Number: 5,789,581
[45] Date of Patent: Aug. 4, 1998

[54] PROCESS FOR OBTAINING MALONYL ISOFLAVONE GLYCOSIDES AND OBTAINING ISOFLAVONE GLYCOSIDES OR ISOFLAVONE AGLYCONS FROM MALONYL ISOFLAVONE GLYCOSIDES

[75] Inventors: Masaru Matsuura; Akio Obata; Kouichiro Tobe; Nobuyuki Yamaji, all of Noda, Japan

[73] Assignee: Kikkoman Corporation, Noda, Japan

[21] Appl. No.: 630,347

[22] Filed: Apr. 10, 1996

[30] Foreign Application Priority Data

Apr. 14, 1995 [JP] Japan ................. 7-112705

[51] Int. Cl.$^6$ .................. C07G 3/00; C07H 17/00; C07H 1/08
[52] U.S. Cl. .................. 536/128; 536/124; 536/18.5
[58] Field of Search .................. 536/128, 124, 536/18.5

[56] References Cited

U.S. PATENT DOCUMENTS

| | | | |
|---|---|---|---|
| 4,428,876 | 1/1984 | Iwamura | 536/128 |
| 4,557,927 | 12/1985 | Miyake et al. | 536/4.1 |
| 5,141,746 | 8/1992 | Fleury et al. | 514/25 |
| 5,320,949 | 6/1994 | Shen | 435/68.1 |
| 5,554,519 | 9/1996 | Weber et al. | 435/125 |

FOREIGN PATENT DOCUMENTS

| | | |
|---|---|---|
| 4-21670 | 8/1987 | Japan. |
| 3-170495 | 7/1991 | Japan. |

*Primary Examiner*—John Kight
*Assistant Examiner*—Everett White
*Attorney, Agent, or Firm*—Banner & Witcoff, Ltd.

[57] ABSTRACT

A malonylisoflavone glycoside present in soybean is obtained efficiently. In addition, the corresponding isoflavone glycoside and aglycone are obtained from the malonylisoflavone glycoside. An aqueous extract of soybean is adsorbed on an adsorbent, and eluted with an aqueous alcohol solution.

10 Claims, No Drawings

5,789,581

PROCESS FOR OBTAINING MALONYL ISOFLAVONE GLYCOSIDES AND OBTAINING ISOFLAVONE GLYCOSIDES OR ISOFLAVONE AGLYCONS FROM MALONYL ISOFLAVONE GLYCOSIDES

BACKGROUND OF THE INVENTION

1. Field of the Invention

The present invention relates to a process for obtaining malonylisoflavone glycosides from an aqueous extract of soybean, and to a process for obtaining isoflavone glycosides as well as isoflavone aglycones from the malonylisoflavone glycosides.

2. Related Art

It has hitherto been confirmed that soybean contains isoflavone compounds such as daidzin, glycitin, genistin, acetyldaidzin and acetylgenistin, or their aglycone derivatives such as daidzein, glycitein and genistein, which exhibit a variety of pharmacological effects such as estrogenic activity, anti-bacterial activity, antioxidizing activity and cancerocidal activity.

Furthermore, it has been recently confirmed that malonylisoflavone glycosides such as malonyldaidzin and malonylgenistin represented by the formulae:

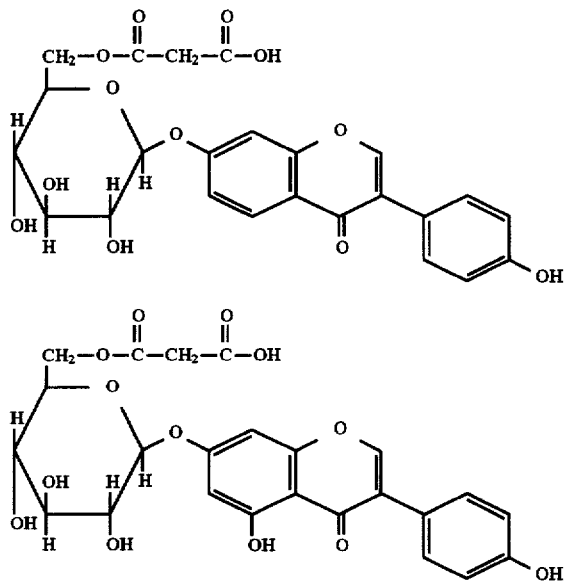

are present in soybean, and it has been proved that these glycoside derivatives comprise the main components of isoflavone compounds in soybean. These malonylisoflavone glycosides are easily soluble in water and exhibit per se anti-oxidizing activity, so that they are anticipated to have pharmacological effects described above from the structural similarity to the afore-mentioned isoflavone and aglycone compounds.

The content of malonylisoflavone glycosides in soybean varies depending on the kinds and harvesting times of soybean and typically specified in Table 1 [J. Agric. Food Chem., 42, 1674 (1994)].

The contents are expressed by microgram per gram of soybean.

TABLE 1

| Soybean (Year) | Malonyldaidzin | Malonylgenistin |
|---|---|---|
| American | | |
| Vinton 81 (1989) | 410 | 958 |
| Vinton 81 (1990) | 300 | 743 |
| Vinton 81 (1991) | 237 | 545 |
| Pioneer 9111 (1989) | 690 | 1756 |
| Pioneer 9202 (1989) | 630 | 1705 |
| Prize (1989) | 709 | 1342 |
| HP204 (1989) | 345 | 915 |
| LS301 (1989) | 752 | 1558 |
| KL72 (1989) | 198 | 1042 |
| Strayer 2233 (1989) | 385 | 883 |
| Japanese | | |
| Keburi (1991) | 562 | 1232 |
| Keburi (1992) | 322 | 670 |
| Kuro daizu (1991) | 375 | 1187 |
| Kuro daizu (1992) | 222 | 717 |
| Raiden (1991) | 407 | 1191 |
| Raiden (1992) | 242 | 723 |

In addition, the malonylisoflavone glycosides can be easily treated with an alkali or by heating to cut the ester linkage between malonyl moiety and glucopyranosyl moiety and to form isoflavone glycosides such as daidzin and genistin, which are further treated with an acid or an enzyme to form isoflavone aglycones. In other words, the malonylisoflavone glycosides can also be used as the raw materials for obtaining daidzin or genistin.

A method for preparing a malonylisoflavone glycoside from soybean is described for example in Japanese Patent Application Kokai (Laid-Open) No. 3-170495, in which ground soybean is extracted with an alcohol, and the extract is further extracted with water incompatible organic solvents via several steps to give the product.

This method has however defects of complicated operation, difficulty of purification due to the contamination of oleophilic components during the alcohol extraction as well as low yields of 5–20%.

SUMMARY OF THE INVENTION

In consideration of the current situations, the present inventors have studied on the processes for obtaining a malonylisoflavone glycoside from soybean in a simple operation. As a result, they have found that the extraction of soybean with water makes possible of the selective extraction of the malonylisoflavone glycoside relatively easily, that when the aqueous extract is directly put into contact with an adsorbent, the malonylisoflavone glycoside in the extract is easily adsorbed on the adsorbent, which is then rinsed with an aqueous alcohol solution to elute the malonylisoflavone glycoside in efficiency, and that the malonylisoflavone glycoside may be treated for example with an alkali to convert it easily into an isoflavone glycoside or an isoflavone aglycone. The present invention has thus been accomplished.

DETAILED DESCRIPTION OF THE INVENTION

The present invention is described in detail below.

Raw materials for malonylisoflavone glycosides include whole soybean, dehulled soybean, and defatted soybean, and aqueous extracts thereof are usually used as the raw material. The extract is the one which is obtained by soaking whole soybeans, dehulled soybeans, or defatted soybeans in water at 20°–80° C. for 2–30 hours, but dehulled soybeans or defatted soybeans are preferably used because of low extraction rate in whole soybeans.

Naturally, waste water (soaked water of soybeans or whey of tofu) resulting in the preparation of tofu or soybean milk can also be used effectively.

As a preferred embodiment for obtaining an aqueous extract of soybean, dehulled soybeans are soaked in water which has been adjusted to pH of 10.0 or less, preferably 7.5–9.0 with sodium hydroxide at a temperature of 45°–65° C. for 2–4 hours, and the soaked soybeans are removed to give the soaking water as the aqueous extract.

In this case, if the soaking water has pH of 10.0 or more, the yield of a malonylisoflavone glycoside is decreased because the malonylisoflavone glycoside is decomposed and an isoflavone glycoside is formed therefrom.

While it is advantageous to soak soybeans in water at a higher temperature in order to increase the extraction rate of the soybean components, the malonylisoflavone glycoside will be decomposed at a temperature of 70° C. or more. Thus, it is suitable to conduct a soaking at a temperature of 45°–65° C. in view of the balance of the extraction rate and the decomposition rate.

The defatted soybean used as a raw material is appropriately a low-denatured defatted soybean, or it may be a soybean whey which is obtained by directly soaking the soybean in water for extraction, or by extracting the ground low-denatured defatted soybean with water or an aqueous alkali to remove insoluble residues and precipitating the extract with an acid at pH of about 4.3 with hydrochloric acid to remove the separated soybean protein.

The filtrate of such an extract of the soybean, from which protein has been removed with an ultrafiltration membrane according to necessities, or the supernatant of the soybean whey, which has been adjusted to pH of about 4.3 with hydrochloric acid to precipitate proteins dissolved in the extract, is put into contact with an adsorbent.

The filtrate or the supernatant is put into contact with an adsorbent directly or after the filtrate or the supernatant is adjusted to pH of about 8.0 with sodium hydroxide.

These methods are advantageous in that the adsorbed amount per adsorbent is increased in the former method, and the malonylisoflavone glycoside and the isoflavone glycoside are easily separated in the latter method.

In either of these methods, the adsorbent used includes for example a synthetic adsorbent, active carbon or alumina, specifically DIAION HP-20 (manufactured by Mitsubishi Chemical Corp.), Purified SHIRASAGI ACTIVE CARBON (manufactured by Takeda Chemical Industries, Ltd.), Active Alumina (manufactured by Wako Pure Chemical Industries, Ltd.), or the like.

Contact may be carried out by the conventional methods such as a batch method or a column method, for example the extract may be put into contact with the adsorbent by flowing through a column in which the adsorbent has been packed, and thus most of the malonylisoflavone glycoside in the extract is adsorbed on the adsorbent.

Next, the malonylisoflavone glycoside adsorbed on the adsorbent is eluted with an aqueous alcohol solution or an aqueous alkaline alcohol solution.

The solution thus obtained is concentrated under reduced pressure, or concentrated under reduced pressure and lyophilized to give a dry powder of the malonylisoflavone glycoside.

The concentrated or the dry crude powder is a mixture of malonyldaidzin and malonylgenistin, which can be fractionally separated by reverse phase chromatography. By way of example, the concentrate is flown through a column in which an ODS resin (manufactured by YAMAMURA KAGAKU) is packed to adsorb the malonylisoflavone glycoside, which is eluted with an aqueous alcohol solution to fractionate malonyldaidzin and malonylgenistin, and these fractions are concentrated under reduced pressure and then lyophilized to give dry powders of malonyldaidzin and malonylgenistin, respectively.

In this connection, malonyldaidzin and malonylgenistin are preferably obtained efficiently by the following method. That is, soybean extract is put into contact with an adsorbent in the same manner as above, elution is conducted with various concentrations of an aqueous alcohol solution to fractionate roughly malonyldaidzin and malonylgenistin, and these fractions are further purified with an ODS resin column.

According to the present invention, the malonylisoflavone glycoside, or malonyldaidzin and malonylgenistin can be obtained fractionatingly from the extract of soybean in a simple procedure, and an isoflavone glycoside as well as an isoflavone aglycone can also be obtained starting from the above described compounds by the alkali treatment or the like.

By way of example, a solution having the malonylisoflavone glycoside dissolved therein is adjusted to pH of 8–13 with an alkali such as ammonia, sodium hydroxide and sodium carbonate and left standing for 0.5 hour or more to convert the malonylisoflavone glycoside into an isoflavone glycoside. The treatment with an alkali having a higher pH results in a higher conversion. In addition, the malonylisoflavone glycoside is converted into the isoflavone glycoside by heating a solution of the malonylisoflavone glycoside at 70°–150° C. for 0.5–12 hours. Heating at a higher temperature for a longer period results in a higher conversion rate. The conversion rate can be further increased with a combination of pH of the solution and the heating temperature.

The isoflavone glycoside thus converted is adsorbed on an ODS resin and eluted with an aqueous alcohol solution, and the eluate is concentrated under reduced pressure and lyophilized to give the isoflavone glycoside in a high purity.

The isoflavone glycoside thus obtained can be converted into an isoflavone aglycone by the further treatment with an acid or an enzyme.

In the case of the acid treatment, for example, a solution of the isoflavone glycoside in a mixture of hydrochloric acid (12N) and methanol at a ratio of 1:4.5 is heated under reflux at at least 70° C. for about 6 hours, cooled, and diluted with water to deposit the products. The products are collected by filtration, washed with water, dissolved in hot ethanol, diluted with water in a ratio of 4 to 6 of the ethanol solution. The mixture is left standing at room temperature to crystallize the corresponding aglycone.

In this acid treatment, the aglycone is also obtained even if the malonylisoflavone glycoside is used as the raw material.

In the case of the enzyme treatment, the isoflavone glycoside is dispersed in a solution of β-glucosidase derived from soybean in 1/10M phosphate buffer (pH 5.0). After reaction at 50° C. for about 6 hours, the reaction mixture is adsorbed on an ODS resin column, eluted with an aqueous alcohol solution, concentrated under reduced pressure, and lyophilized to give an isoflavone aglycone as a purified product.

EXAMPLE

The present invention is specifically described by the following examples.

Example 1

Dehulled soybean (3 kg) obtained by heating a commercially available American soybean (IOM) to a soybean temperature of about 80° C. under the atmosphere of 120° C. or more, dividing in two with a rubber roll, cooling the divided soybean, and removing the hulls, was soaked into and extracted with 30 liters of water heated to 50° C. for 2 hours with adjusting pH to 8.0 to give 25 liters of an extract. The extract was adjusted to pH 4.0 with concentrated hydrochloric acid, left standing for 2 hours, and decanted to give 20 liters of a supernatant, which was next flown through a column (5×21.5 cm, 420 ml) having a synthetic adsorbent DIAION HP-20 (manufactured by Mitsubishi Kagaku) packed therein at a flow rate of 1 liter/hour to adsorb the malonylisoflavone glycoside, and washed with 2 liters of distilled water.

Next, elution was carried out with 2 liters of a 5% aqueous ethanol solution, 3 liters of 10%, 20%, 30% and 40% aqueous ethanol solutions, respectively, and 2 liters of a 50% aqueous ethanol solution.

Elutes was collected in 1 liter fractions, analyzed by high performance liquid chromatography (HPLC), separated into a malonyldaidzin fraction and a malonylgenistin fraction, which were concentrated under reduced pressure at a temperature of 50° C. to a volume of about 2 liters to give concentrates containing 1.61 g of malonyldaidzin and 1.76 g of malonylgenistin, respectively.

Purification of Malonyldaidzin

The malonyldaidzin containing concentrate was next adjusted to pH 8.0 with 2N NaOH, flown through a column (4×16 cm, 200 ml) packed with a synthetic resin, ODS resin at a flow rate of 30 ml/min, and washed with 0.5 liter of distilled water. Next, elution was carried out with 2 liters of a 5% aqueous ethanol solution, and fractions containing the preferred product were collected, concentrated, and lyophilized to give 1.15 g of the sodium salt of malonyldaidzin.

Purification of Malonylgenistin

Also, the malonyldaidzin containing concentrate was adjusted to pH 8.0 with 2N NaOH, flown through a column packed with a synthetic resin, ODS resin in the similar manner, and washed with 0.5 liter of distilled water. Next, elution was carried out with 2 liters of a 10% aqueous ethanol solution, and fractions containing the preferred product were collected, concentrated, and lyophilized to give 1.15 g of the sodium salt of malonylgenistin.

$^1$H- and $^{13}$C-NMR spectra of malonyldaidzin and malonylgenistin thus obtained were accorded with those described in Agric. Biol. Chem., 55 (9), 2227 (1991). In addition, dehulled soybean used as the raw material was analyzed on malonylisoflavone glycoside according to the method described by Wang et al. in J. Agric. Food Chem., 42, 1666 (1994).

That is, dehulled soybeans were ground, and 2.0 g of the sample which passed through a screen of 40 mesh was mixed with 100 ml of acetonitrile and 20 ml of 0.1N HCl. After stirring the mixture at room temperature for 2 hours, it was filtered through a Toyo Filter Paper No. 2, and the filtrate was concentrated to dryness in a rotary evaporator at a temperature of 30° C. or less.

The residue was dissolved in 10 ml of 80% methanol, filtered through a membrane filter, and a 20 μl of the filtrate was subjected to HPLC analysis. Average values of three runs of the analysis were 68.8 mg for malonyldaidzin and 103.3 mg for malonylgenistin per 100 g of the dehulled soybeans.

From these results, the yields of malonyldaidzin and malonylgenistin in Example 1 were determined to be 56% and 44%, respectively.

Example 2

Warm water extract of dehulled soybeans (20 liters) obtained in the same manner as in Example 1 was adjusted to pH 4.0 with hydrochloric acid, left standing for 2 hours, mixed with a filtration aid (RADIOLITE # 500, manufactured by SHOWA KAGAKU), and filtered under reduced pressure through a Buechner funnel. The filtrate was next flown through a column (5×22 cm, 430 ml) having active carbon (Purified SHIRASAGI, for chromatography, manufactured by Takeda Chemical Industries, Ltd.) packed therein at a flow rate of 1.5 liter/hour to adsorb the malonylisoflavone glycoside, and washed with 3 liters of 1% aqueous ammonia.

Next, elution was carried out with 5 liters of a 50% aqueous ethanol solution containing 1% ammonia, and the elute obtained was concentrated under reduced pressure at 50° C. to give 500 ml of a concentrate containing 1.23 g of malonyldaidzin and 1.05 g of malonyl genistin.

The concentrate was adjusted to pH 8.0 with 2N sodium hydroxide, flown through a column (4×24 cm, 300 ml) packed with an ODS resin at a flow rate of 30 ml/min, and washed with 0.5 liter of distilled water. Next, elution was carried out with 2 liters of 2%, 5% and 10% aqueous ethanol solutions, respectively. The malonyldaidzin fraction was obtained from the fractions eluted with the 5% aqueous ethanol solution, and the malonylgenistin fraction was obtained from the fractions eluted with the 10% aqueous ethanol solution. Each of these fractions was concentrated under reduced pressure at 50° C., and lyophilized to give 652 mg of the sodium salt of malonyldaidzin and 412 mg of the sodium salt of malonylgenistin.

Example 3

To low-denatured defatted soybeans (manufactured by NISSHIN OIL MILLS LTD., 3 kg) was added 30 liters of water, and the mixture was adjusted to pH 7.0 with a 1N NaOH solution, stirred at 25° C. for 2 hours, and centrifuged to remove solids. The supernatant was adjusted to pH 4.5 with a 1N HCl solution, and centrifuged to give 24 liters of a whey portion containing 1.1 g of malonyldaidzin and 0.8 g of malonylgenistin. The whey portion was purified in the same manner as in Example 1 to give the sodium salts of malonyldaidzin and malonylgenistin in the yields of 0.68 g and 0.44 g, respectively.

Example 4

To low-denatured defatted soybean (manufactured by NISSHIN OIL MILLS LTD., 3 kg) was added 30 liters of water, and the mixture was adjusted to pH 7.0 with a 1N NaOH solution, stirred at 25° C. for 2 hours, and centrifuged to remove solids. The supernatant was adjusted to pH 4.5 with a 1N HCl solution, and centrifuged to give 24 liters of a whey portion. The whey portion was flown through a column having a synthetic adsorbent, DIAION HP-20, packed therein to adsorb the malonylisoflavone glycoside, and elution, fractionation, concentration and purification were conducted in the same way as in Example 1 to give the sodium salts of malonyldaidzin and malonylgenistin in the yields of 0.68 g and 0.44 g, respectively.

Example 5

To low-denatured defatted soybeans (manufactured by NISSHIN OIL MILLS LTD., 3 kg) was added 30 liters of water, and the mixture was adjusted to pH 8.0 with a 1N NaOH solution, stirred at 25° C. for 2 hours, and centrifuged to remove solids. The supernatant (22.5 liters) thus obtained was adjusted to pH 4.5 with a 1N HCl solution, and centrifuged to give 22 liters of a whey portion. The whey portion was flown through a column having a synthetic adsorbent, DIAION HP-20, packed therein to adsorb the malonylisoflavone glycoside, and elution, fractionation, concentration and purification were conducted in the same way as in Example 1 to give the sodium salts of malonyldaidzin and malonylgenistin in the yields of 0.53 g and 0.32 g, respectively.

Example 6

Each of 1 g samples of the sodium salts of malonyldaidzin and malonylgenistin obtained in the same manner as in Example 1 was dissolved in 500 ml of distilled water, and heated in a device equipped with a condenser in a boiling water for 5 hours. Analysis by HPLC proved that the conversion of the salt into the corresponding glycoside was 90% or more. The product was purified on a column having an ODS resin packed therein to give the corresponding glycosides, daidzin and genistin in the yields of 0.73 g and 0.67 g, respectively.

Example 7

Each of 2 g samples of the sodium salts of malonyldaidzin and malonylgenistin obtained in the same manner as in Example 1 was dissolved in 1,000 ml of distilled water, and adjusted to pH 10 with 1N NaOH. The solution was left standing at room temperature for 24 hours. Analysis by HPLC proved that the conversion of the salt into the corresponding glycoside was 90% or more. The product was neutralized with hydrochloric acid and purified on a column having an ODS resin packed therein in the same manner as in Example 4 to give the corresponding glycosides, daidzin and genistin in the yields of 1.36 g and 1.30 g, respectively.

Example 8

To each of 1 g samples of daidzin and genistin obtained in Example 7 were added 45 ml of methanol and 10 ml of 12N HCl, and the glycoside was decomposed under reflux for 6 hours. After cooling, the reaction mixture was diluted with water, and the solid product was collected by filtration, washed with water, dissolved in 90 ml of a 80% ethanol solution, filtered through a filter paper to give a supernatant. The supernatant was left standing at room temperature to deposit a crystalline product. The mixture was left standing overnight, and the crystals were collected and dried to give daidzein and genistein in the yields of 410 mg and 440 mg, respectively.

The isoflavone glycosides and the isoflavone aglycones obtained in Examples 6–8 have the same physical properties as those of the authentic samples (available from FUNAKOSHI K.K.).

According to the present invention, it is possible to obtain efficiently in a simple procedure from an aqueous extract of soybean the malonylisoflavone glycosides, from which the isoflavone glycosides as well as isoflavone aglycones are also obtained by treatments with for example an alkali and the like.

What is claimed is:

1. A process for obtaining a malonylisoflavone glycoside which comprises contacting a whey produced during preparation of isolated soybean protein with an absorbent to absorb the malonylisoflavone glycoside in the whey, and then eluting the glycoside with an aqueous alcohol solution.

2. A process for obtaining an isoflavone glycoside comprising treating a malonylisoflavone glycoside obtained according to the process of claim 1 with heat and/or an alkali to give an isoflavone glycoside.

3. A process according to claim 2, wherein a solution of a malonylisoflavone glycoside is heated at 70° C. or more to give an isoflavone glycoside.

4. A process according to claim 2, wherein a solution of a malonylisoflavone glycoside is treated with an alkali at pH 8 or more.

5. A process for obtaining an isoflavone aglycone comprising treating a malonylisoflavone glycoside obtained according to the process of claim 1 with heat and/or an alkali to give an isoflavone glycoside, which is treated with an acid or an enzyme to give an isoflavone aglycone.

6. A process according to claim 5, wherein an isoflavone glycoside solution is treated with heat in an aqueous alcohol solution containing dilute hydrochloric acid to give an isoflavone aglycone.

7. A process according to claim 5, wherein an isoflavone glycoside solution is hydrolyzed with β-glucosidase to give an isoflavone aglycone.

8. A process for obtaining an isoflavone aglycone, wherein a malonylisoflavone glycoside solution obtained according to the process of claim 1 is treated with heat directly in an aqueous alcohol solution containing dilute hydrochloric acid to give an isoflavone aglycone.

9. A process according to claim 1, wherein the malonylisoflavone glycoside is malonyldaidzin or malonylgenistin.

10. A process for obtaining a malonylisoflavone glycoside which comprises contacting a whey produced during production of isolated soybean protein with an adsorbent to adsorb the malonylisoflavone glycoside in the whey, and then eluting the glycoside with an aqueous alcohol solution and heating said eluate at a temperature of 70° C. or more to give an isoflavone glycoside.

* * * * *